United States Patent [19]

Vlachakis

[11] 4,275,150

[45] Jun. 23, 1981

[54] RADIOENZYMATIC METHOD FOR ASSAYING NORMETANEPHRINE

[76] Inventor: Nicolas D. Vlachakis, 3515 Landfair Rd., Pasadena, Calif. 91107

[21] Appl. No.: 7,701

[22] Filed: Jan. 30, 1979

[51] Int. Cl.³ .................... G01N 33/48; G01T 1/00; G01N 33/54
[52] U.S. Cl. ............................ 435/7; 23/230 B; 424/1; 424/12
[58] Field of Search .............. 424/1, 12; 23/230 B; 435/7

[56] References Cited

U.S. PATENT DOCUMENTS

| | | | |
|---|---|---|---|
| 4,041,076 | 8/1977 | Avenia et al. | 23/230 B |
| 4,108,973 | 8/1978 | Avenia et al. | 424/1 |

*Primary Examiner*—Benjamin R. Padgett
*Assistant Examiner*—Christine M. Nucker
*Attorney, Agent, or Firm*—William W. Haefliger

[57] ABSTRACT

Normetanephrine, an N-methylatable phenylethanolamine, is converted to its N-methylated, tritiated derivative, metanephrine, utilizing phenylethanolamine-N-methyltransferase as enzyme and tritiated S-adenosyl-L-methionine as methyl donor. The formed tritiated derivative is selectively extracted in organic solvents and separated from other N-methylatable phenylethanolamines by thin layer chromatography. This assay could be used for measurement of normetanephrine in biological systems of patients with hypertension for detection of pheochromocytoma.

11 Claims, 2 Drawing Figures

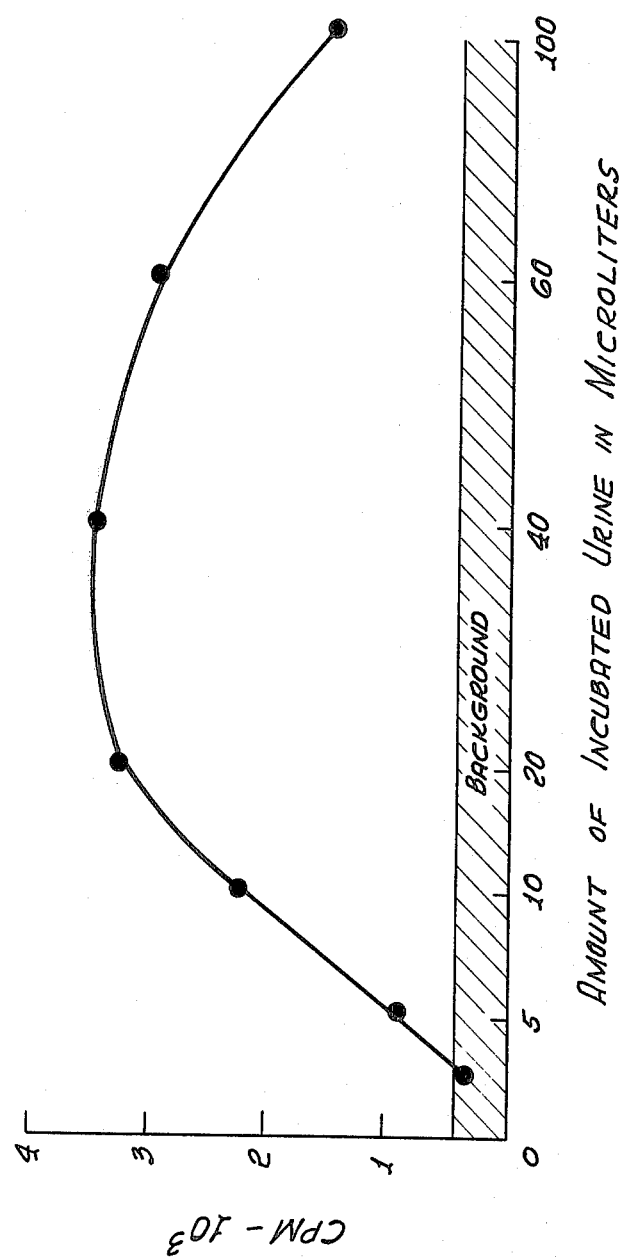
GRAPH 1.

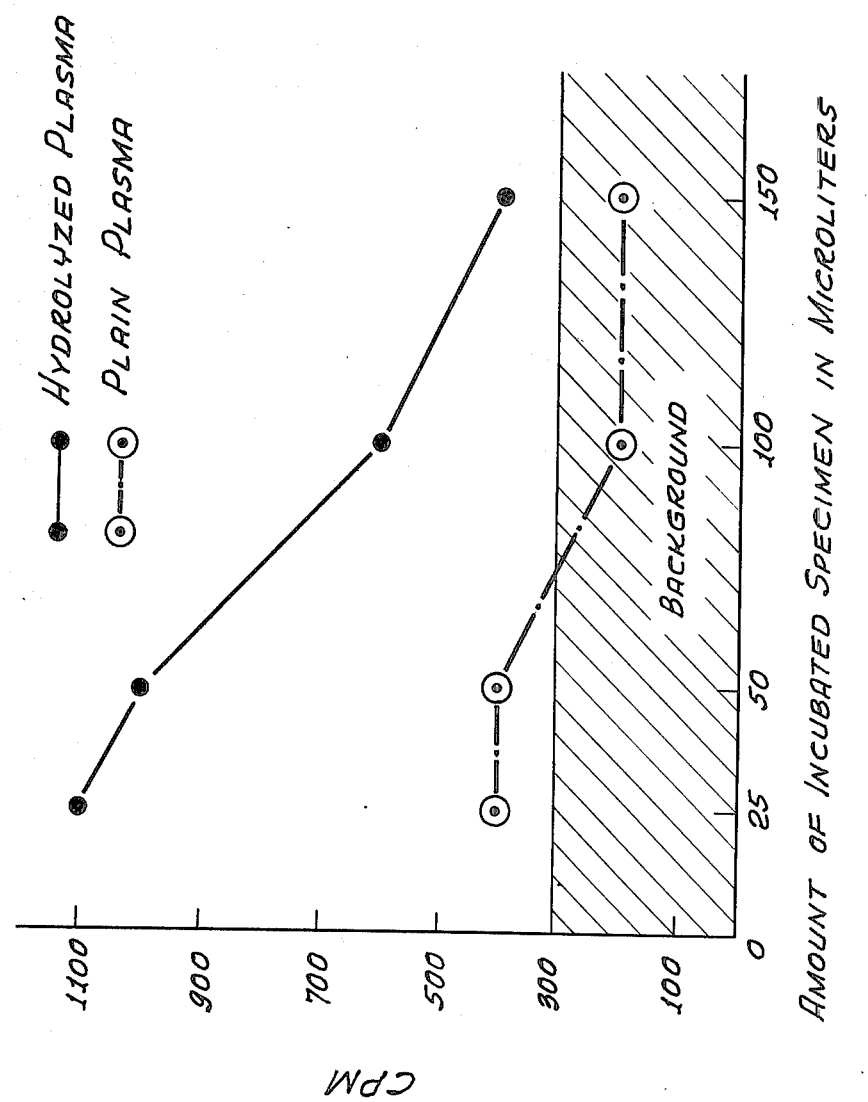
GRAPH 2.

RADIOENZYMATIC METHOD FOR ASSAYING NORMETANEPHRINE

FIELD OF THE INVENTION

The field of art to which the invetion pertains includes the field of a phenylethanolamine assay.

BACKGROUND AND SUMMARY OF THE INVENTION

For a variety of clinical reasons it is desirable to quantatively assay one or more phenylethanolamines found, for example, in urine, in plasma, in brain tissue or the like. For example, the diagnosis of pheochromocytoma has been based upon measurement of the increased plasma or urinary levels of catecholamines and their metabolites such as metanephrine, normetanephrine and 3-methoxy-4-hydroxy-mandelic acid. Such diagnosis is important because these tumors produce a potentially curable form of hypertension, which otherwise is fatal. However, techniques for measurements of urinary catecholamines and catecholamine metabolites are non-specific, laborious, tedious and frequently associated with false positive results. Furthermore, plasma catecholamines may be within normal range, because some tumors may secrete large amounts of pharmacologically inactive metabolites (normetanephrine), but relatively small amounts of free norepinephrine and epinephrine. The measurement of the catecholamine metabolite normetanephrine in plasma should be the best test for detection of pheochromocytoma, since the kidney can directly alter the excretion of metabolites.

Because plasma concentration of free normetanephrine is low and the presence of inhibitors for the enzyme, normetanephrine in plasma cannot be detected. In a particular embodiment, conjugated normetanephrine is deconjugated (liberated) by acidic hydrolysis. Furthermore, a substantial degree of inhibition is overcome by decreasing the amount of incubated plasma to less than 100 microliters. The method is specific and rapid, yielding results in less than three hours while one person could easily perform thirty-six assays in eight hours. The method has particular importance with respect to the detection of normetanephrine in hypertensive patients even during therapy, as no antihypertensive drugs interfere with the assay.

Specifically, a method is provided for assaying an N-methylatable phenylethanolamine in a sample by converting the phenylethanolamine to its N-methylated derivative with a tritiated methyl group, and measuring the radioactivity of the derivative. Conversion can be accomplished by transmethylation, exemplified by reaction with S-adenosyl-L-methionine having a tritiated methyl group and promoted by a transfer enzyme therefor, exemplified by phenylethanolamine-N-methyl-transferase. The target phenylethanolamine typically would be found among a plurality of other N-methylatable phenylethanolamines. Accordingly, the method includes the step of separating the methylated target phenylethanolamine from other N-methylated phenylethanolamines prior to measuring the radioactivity. In a particular embodiment, the separation step comprises isolating the methylated target phenylethanolamine by thin layer chromatography. In a further embodiment, calculation is aided by concurrently processing a duplicate sample but to which has been added a known amount of the target phenylethanolamine, serving as a standard for the calculation. The isolated target derivative can then be combined with a scintillation fluid and its radioactivity measured in liquid scintillation counter.

In a particular embodiment, normetanephrine is assayed in a sample of plasma or urine containing a plurality of other N-methylatable phenylethanolamines. To the sample is added S-adenosyl-L-methionine having a tritiated methyl group, and phenylethanolamine-N-methyl transferase as promoter. The combination is incubated for a time sufficient to transmethylate the normetanephrine with the tritiated methyl group to form tritiated metanephrine. The specificity of the assay is based on the fact that the N-methylated phenylethanolamines have coefficients of extraction and chromatographic characteristics which differ one from the other. Accordingly, the tritiated metanephrine can be separated from other N-methylated phenylethanolamines and its radioactivity measured.

The technique presented by this disclosure is very convenient both to the patient and to laboratory personnel. For example, urine can be collected in any clean container without any preservative and an aliquot can be stored in a freezer until analysis. The assay allows collection of a random urine sample when the patient is hypertensive or symptomatic, with the analysis being conducted even several days later. The assay is sensitive enough to be used as a routine test. For example, one can measure less than 50 picograms of normetanephrine with a variability of about 3.5%, thus providing a specific, rapid and accurate assay for the detection of pheochromocytoma.

These and other objects and advantages of the invention, as well as the details of specific examples, will be more fully understood from the following:

DRAWING DESCRIPTION

FIGS. 1 and 2 are graphs.

DETAILED DESCRIPTION

In assaying for the methylatable phenylethanolamine, the sample to be analyzed can be placed in a test tube and the transmethylating and promoting agents added thereto. The sample can be any material in which is naturally found the excreted target phenylethanolamine, such as urine, plasma, brain tissue, etc. The target phenylethanolamine is the N-methylatable phenylethanolamine normetanephrine.

N-methylation is accomplished by transmethylation using commercially available tritiated S-adenosyl-L-methionine, having one or more hydrogen atoms on its methyl group substituted with tritium ($^3$H), promoted by a transfer enzyme therefor. Such a transfer enzyme is phenylethanolamine-N-methyl-transferase obtainable from the medullary tissue of bovine adrenals, as known to the art. Preferably the sample is buffered e.g. to a pH in range of 8.0–8.5 to facilitate the transmethylation. An internal standard consisting of a known amount of the target phenylethanolamine can be added to a duplicate sample for concurrent processing and blanks can be prepared for concurrent processing made up of the reagents alone without the sample and without the standard. The reaction mixture can be incubated for a time sufficient to assure the completion of reaction, or it can be terminated after a specific length of time, by raising the pH to a level above that which is suitable for transmethylation (e.g., to a pH of 10.0).

The resultant mixture can be subjected to thin film chromotography using known techniques, such as by using an automatic thin layer chromotography multi-spotter, spotting the mixture on silica gel plates. The plates can be developed and dried, and bands corresponding to the N-methylated target phenylethanolamine can be located by inspection for example under short wave ultraviolet light. The target band can be scraped into scintillation vials containing ammonium hydroxide to which scintillation fluid can be added. The vials can then be placed into a liquid scintillation counter and the counts per minute determined. The amount of target phenylethanolamine, as tritiated N-methylated phenylethanolamine, can be determined using the following formula:

$$\frac{CPM_{sample} - CPM_{blank}}{CPM_{(sample+standard)} - CPM_{sample}} \times M = \text{ng/ml of sample}$$

$M$ = amount of incubated specimen

Accordingly, one can determine the counts per minute (CPM) of the sample, the blank, and the sample plus internal standard, and applying the above formula, one can obtain in nanograms the amount of N-methylated phenylethanolamine per milliliter of sample.

The following examples will serve to further illustrate the invention.

EXAMPLE I

Preparation of
Phenylethanolamine-N-Methyl-Transferase (PNMT)

Thirty-three grams of medullary tissue were dissected from 15 fresh bovine adrenals and homogenized in 280 ml of isotonic KCl. The homogenate was centrifuged at 40.000 g for one hour and the supernatant was filtered and recentrifuged at 100.000 g for one hour. To 250 ml of the supernatant were added 5 ml of 0.05 M sodium phosphate buffer, pH 7.5 and 44 g of solid ammonium sulfate. Another 19.8 g of ammonium sulfate per 100 ml was added. The supernatant was discarded and the precipitate resuspended in 100 ml of 55 percent saturated ammonium sulfate, 25 ml of 0.0125 M sodium phosphate was added. The solution was recentrifuged and for each 100 ml of supernatant, 17 g of ammonium sulfate was added. After centrifugation the precipitate was resuspended in 50 ml of 0.005 M tris-HCl, pH 7.4, containing 0.1 mM dithiothreitol and dialyzed in four liters of the buffer with four changed in a 16 hour period. The dialyzed enzyme was then centrifuged at 40.000 g for 10 minutes and frozen in small aliquots. The protein concentration was eight micrograms per liter.

Sample Preparation

In a clean small container without preservatives, urine was collected and brought to the laboratory. One ml of urine was transferred into a plastic tube and stored in a freezer at −20° C. until analysis. Less than one ml of blood is drawn in a syringe and transferred into a clean tube and brought to the laboratory or sent by mail since specimen left in room temperature for 24 to 48 hours did not affect the results. Plasma normetanephrine was determined after being deconjugated with acidic hydrolysis. On the day of the assay sample was thawed, pH was decreased to 1.0 by adding 10 percent of 5 N perchloric acid (v/v) and boiled for 20 minutes in a boiling water bath. The specimen was centrifuged at 800 g for 5 minutes and the supernatant is transferred to another tube, pH is brought to 8.4 by adding 20 percent of 5 N tris-base, pH 10.8 (v/v).

Assay Procedure

Ten microliters of urine or 25 microliters of hydrolyzed plasma were placed into a 13×100 mm disposable tube and to that was added: 10 microliters of buffer, pH 8.6 (consisting of Tris-HCl 1 M) and 5 microliters of S-adenosyl-L-methionine ($^3$H-SAME, a commercially available material obtained from New England Nuclear Corporation) containing 2.5 μCi of $^3$H. The reaction was initiated by addition of 15 microliters of PNMT. Internal standards consisting of 0.5 ng of normetanephrine (NMN) were added to another set of tubes along with 10 microliters of urine or 25 microliters of hydrolyzed plasma and the incubation mixture. Blanks were prepared by omission of NMN and sample. The reaction mixture was incubated for 60 minutes at 37° C. in a shaking water bath. The reaction was terminated by adding 150 microliters of sodium borate buffer, pH 11.0. To facilitate locating chromatography bands, 0.5 μmole each of unlabelled NMN, MN and synephrine (N-methyl-octopamine) were added. The N-methylated derivatives were extracted into 2 ml toluene: isoamyl alcohol (3:2, v/v) by mixing on a vortex for 30 seconds. The tubes were centrifuged at 800 g for 2 minutes and the organic phase was transferred (after quick freeze in a dry-ice-acetone bath) into a 13-ml conical glass centrifuge tube containing 150 microliters of 0.1 N acetic acid. The tubes were vigorously vortexed for 30 seconds, centrifuged at 800 g for 2 minutes and the supernatant was aspirated off. The acetic acid was transferred to 250 microliter syringes, and by using an automatic thin layer chromatography multispotter, it was spotted on silica gel plates within 15 minutes. The plates were developed in a tank containing tert. amyl alcohol:benzene:methylamine (60:20:30) for 60 minutes. The plates were subsequently dried rapidly in air and the bands corresponding to NMN, metanephrine (MN) and synephrine were located by inspection under short-wave ultraviolet light. The MN bands were scraped into scintillation vials containing 1 ml of 1 M NH$_4$OH. After gently shaking for 10 seconds, 10 mls of a scintillation fluid (sold commercially by New England Nuclear under the name Aquasol) was added and the vials were placed into a liquic scintillation counter. The amount of endogenous NMN, contained in the MN band as $^3$H-MN was calculated as follows:

$$\frac{CPM_{sample} - CPM_{blank}}{CPM_{(sample+standard)} - CPM_{sample}} \times M = \text{ng/ml of sample}$$

$M$ = amount of incubated specimen

The creatinine content of the urine was determined and results were expressed as ng NMN per mg creatinine.

Results

The following tables list normetanephrine concentration in urine and plasma assayed in normal volunteers and patients with hypertension and other diseases, following the above procedure. The results are expressed as Mean±the Standard Error of the Mean.

As shown in Table I, in Group I, urinary NMN excretion ranged from 5.8 to 53 ng per mg creatinine (mean of 24±2.6 standard error) in 22 ambulatory normotensive and healthy subjects during the morning hours.

TABLE I

| Group | Number of Cases | Age Years | Sex | Normetanephrine ng per mg of Creatinine | Diagnosis |
|---|---|---|---|---|---|
| I | 22 | 31 ± 2.2 | 14 M 8 F | 24 ± 2.6 | Normotensive and healthy subjects |
| II | 15 | 50 ± 3.6 | 11 M 4 F | 27 ± 5.4 | Patients from the general Medical Ward* |
| III | 5 | 49 ± 6 | 3 M 2 F | 270 ± 154 | Within 24 hours following a major thoracic or abdominal surgery |
| IV | 3 | 35 ± 7 | 1 M 2 F | 2738 ± 1580 | Patients with pheochromocytoma confirmed at surgery |

*Includes patients with hypertension on treatment, cerebrovascular accident in coma, gastric bleeding, acute respiratory failure with intratracheal incubation and other diseases on treatment.

In Group II, 15 patients with various medical problems (including primary hypertension), receiving different medications, had NMN ranging from 7.8 to 92 ng per mg creatinine (mean of 27±5.4 standard error). Although some of these medications (reserpine and guanethidine) could decrease urinary metanephrines, they did not interfere with the assay. In Group III, during the first 24 hours following major abdominal and thoracic surgery on five patients, NMN increased substantially, ranging from 81 to 882 ng per mg creatinine (mean of 270±154 standard error), but did not reach values obtained in patients with pheochromocytoma. In Group IV, the urinary NMN in 3 patients with pheochromocytoma, confirmed at surgery, ranged from 1,200 to 5,714 ng per mg creatinine (mean of 2738±1580 standard error). Vanillylmandelic acid excretion was within normal limits in one patient with pheochromocytoma.

EXAMPLE II

To demonstrate the assay substrate specificity, assays were conducted as in Example I using the solvent system of that Example but in which the sample was normetanephrine and in which there was added to individual tubes an equal amount of another phenylethanolamine. Thus, in one tube one ng of normetanephrine alone was used while in the other tubes they were added to one ng of normetanephrine an equal amount of a catecholamine, a catecholamine metabolite, tyramine or octopamine. After incubation and thin layer chromatography separation, as in Example I, the results shown in Table II were found.

TABLE II

| Assay Substrate Specificity | |
|---|---|
| Substrate | CPM |
| Normetanephrine | 7035 |
| Metanephrine | 6800 |
| Norepinephrine | 6020 |
| Epinephrine | 6066 |
| Dopamine | 7267 |
| Methoxytyramine | 6935 |
| Octopamine | 6896 |
| Tyramine | 7096 |
| Synephrine | 6978 |

TABLE II-continued

| Assay Substrate Specificity | |
|---|---|
| Substrate | CPM |
| Homovanilic acid | 6500 |
| Vanillylamndelic acid | 6647 |
| Dihydroxyphenylalanine | 6785 |

Referring to Table II, the addition of an equal amount of each of various listed phenylethanolamines did not exert any substantial effect on the CPM found. In 60 minutes, N-methylated normetanephrine exhibited a relative flow (rf) value of 0.47 and was completely separated from other potential PNMT substrates. Octopamine was N-methylated to N-methyl-octopamine (synephrine), but synephrine exhibited a rf value of 0.59 and did not increase the CPM for the normetanephrine. However, as indicated in Example I, the addition of cold synephrine to the assay together with normetanephrine and metanephrine carriers, permits a better visualization and delineation of the corresponding spots on chromatographic plates, and avoidance of interference.

EXAMPLES III AND IV

The procedure of Example I can be followed but in place of the urine sample one can use a hydrolyzed plasma sample or a sample of brain tissue.

TABLE III

Total Plasma Normetanephrine Concentration in Normal Volunteers, Primary Hypertension and Patients with Pheochromocytoma

| Group | Number of Cases | Age (Years) | Sex M=male F=female | Total normetanephrine ng per ml of plasma |
|---|---|---|---|---|
| Normotensive | 10 | 43 ± 2 | 6 M, 4 F | 1.2 ± 0.1 |
| Primary hypertensive | 25 | 45 ± 2 | 18 M, 7 F | 2.5 ± 0.2 |
| Pheochromocytoma | 4 | 59 ± 7 | 1 M, 3 F | 188 ± 90 |

In Table III are included levels of plasma normetanephrine in the recumbent position in 10 normal subjects, in 25 patients with primary hypertension and in 4 patients with pheochromocytoma confirmed at surgery. One patient (L. J., Male/52 years old) had a right adrenal pheochromocytoma removed at surgery. He was hypertensive before surgery with very high levels of urinary VMA and catecholamines. The second patient (D. D., Female/44 years) had a bilateral adrenal pheochromocytoma removed at surgery. She was hypertensive with elevated urinary VMA, but normal urinary catecholamines. Urinary combined metanephrines were 2.36 ng per mg of creatinine (normal range 0.001–0.9). The third patient (F. D., Female/78 years) had a left adrenal pheochromocytoma removed at surgery. She was hypertensive with very high plasma and urinary catecholamines and catecholamine metabolites. The fourth patient (A.M., Female/62 years) had a very large (3.4 kg) right adrenal pheochromocytoma removed at surgery. She was consistently normotensive with a hypertensive crisis during intravenous pyelography. Her plasma norepinephrine was 740 pg/ml in the recumbent position and 760 pg/ml in the upright, both values being within ranges found in patients with primary hypertension. However, urinary VMA and metanephrines were very elevated.

In various experiments, it was found that excellent linearity of product forms from 100 pg to at least 10 ng when NMN was added either in distilled water or urine or plasma. However, there was 40 to 45% inhibition of the enzyme by urine when compared to water, increasing progressively with the amount of urine (see Graph I). The smallest inhibition was obtained with 10 microliters of urine, which could be decreased further by increasing the incubation period or the amount of PMNT or diluting the urine. The addition of different chelating agents such as EDTA, EGTA or $MgCl_2$, or antioxidants such as glutathione or dithiothreitol did not affect inhibition. Although urine inhibition decreases sensitivity, it is not a serious decrease in view of the fact that 10 microliters of any casual urine from normal people gave at least 3–6 times the CPM of the blank. The incubation of plain plasma at various quantities, did not consistently yield counts above the blank. On the other hand, the incubation of 25 microliters of hydrolyzed plasma (Graph II), produced a three- to sixfold increase of the CPM above the blank and permitted a comfortable measurement of normetanephrine in plasma, which has never been measured before by any methodology. However, there was an inhibition of the enzyme which increased progressively with the amount of incubated sample. The day to day variability of the assay as tested from the variability of the internal standard was 3.5%.

I claim:

1. A method for assaying normetanephrine in a sample selected from the group which consists of plasma, urine and tissue, the method comprising converting said normetanephrine in the sample to its N-methylated derivative with a tritiated methyl group and measuring the radioactivity of said derivative.

2. The method of claim 1 in which said normetanephrine is converted to its N-methylated derivative by transmethylation.

3. The method of claim 2 in which said transmethylation is from S-adenosyl-L-methionine (SAM) having a tritiated methyl group.

4. The method of claim 3 in which said transmethylation is promoted by a transfer enzyme therefor.

5. The method of claim 4 in which said transfer enzyme is phenylethanolamine-N-methyl-transferase (PNMT).

6. The method of claim 1 wherein the sample consists of hydrolysed plasma, and the amount of sample assayed is less than about 100 $\mu l$.

7. The method of claim 1 wherein the sample consists of urine, and the amount of sample assayed in less than about 100 $\mu l$.

8. The method of claim 1 wherein the sample consists of tissue.

9. The method of claim 1 in which said N-methylated derivative is combined with a scintillation fluid and said radioactivity is measured in a liquid scintillation counter.

10. The method of claim 5 wherein said sample, SAM and PNMT form a mix, and including the step of incubating said mix for a time sufficient to transmethylate said normetanephrine with said tritiated methyl group to form tritiated methanephrine.

11. The method of claim 10 in which said methanephrine is combined with scintillation fluid and said radioactivity is measured in a liquid scintillation counter.

* * * * *